(12) United States Patent
MacKinnon et al.

(10) Patent No.: US 9,557,198 B2
(45) Date of Patent: Jan. 31, 2017

(54) SMART TILES

(71) Applicants: Richard MacKinnon, Charlottetown (CA); Jianwen Jiang, Beijing (CN)

(72) Inventors: Richard MacKinnon, Charlottetown (CA); Jianwen Jiang, Beijing (CN)

( * ) Notice: Subject to any disclaimer, the term of this patent is extended or adjusted under 35 U.S.C. 154(b) by 731 days.

(21) Appl. No.: 13/862,414

(22) Filed: Apr. 13, 2013

(65) Prior Publication Data
US 2014/0307118 A1    Oct. 16, 2014

(51) Int. Cl.
*G01L 1/00* (2006.01)
*G01D 21/00* (2006.01)
*G01L 19/08* (2006.01)

(52) U.S. Cl.
CPC ............. *G01D 21/00* (2013.01); *G01L 19/086* (2013.01)

(58) Field of Classification Search
CPC ............ G01L 1/00; G01L 1/04; G01L 19/086; A61B 5/103; A61B 5/1038; A61B 5/11; A61B 5/112
See application file for complete search history.

(56) References Cited

PUBLICATIONS

Leusmann et al., Your Floor Knows Where You Are: Sensing and Acquisition of Movement Data, 2011, 12th IEEE International Conference on Mobile Data Management, pp. 61-66.*

* cited by examiner

*Primary Examiner* — Toan Le
(74) *Attorney, Agent, or Firm* — Seattle Patent Group LLC; James Haugen

(57) ABSTRACT

The instant application discloses, among other things, techniques to allow multiple tiles containing various types of sensors to be connected via a network to a number of other tiles and a computer, with automatic virtual orientation of the tiles and fast data transmission. Data may be collected by a central processor from four quarter tiles and transmitted to the computer for analysis. Information obtained from the analysis may include, but is not limited to, gait analysis, identity of people on a floor, and safety issues (detecting someone has fallen, for example).

6 Claims, 5 Drawing Sheets

SMART TILES

FIELD

This disclosure relates to Smart Tiles.

BACKGROUND

Pressure measuring mats are used for a variety of purposes, including gait analysis and fall detection. A grid of pressure measuring sensors may be embedded in a mat, with the sensors electrically coupled to a computer. The computer may then display an image of the readings from the sensors, or may do an analysis of the values over time.

SUMMARY

The instant application discloses, among other things, techniques to allow multiple tiles containing various types of sensors to be connected via a network to a number of other tiles and a computer, with automatic virtual orientation of the tiles and fast data transmission.

Data may be collected by a central processor from four quarter tiles and transmitted to the computer for analysis. Information obtained from the analysis may include, but is not limited to, gait analysis, identity of people on a floor, and safety issues (detecting someone has fallen, for example).

DETAILED DESCRIPTION

Figure 1:
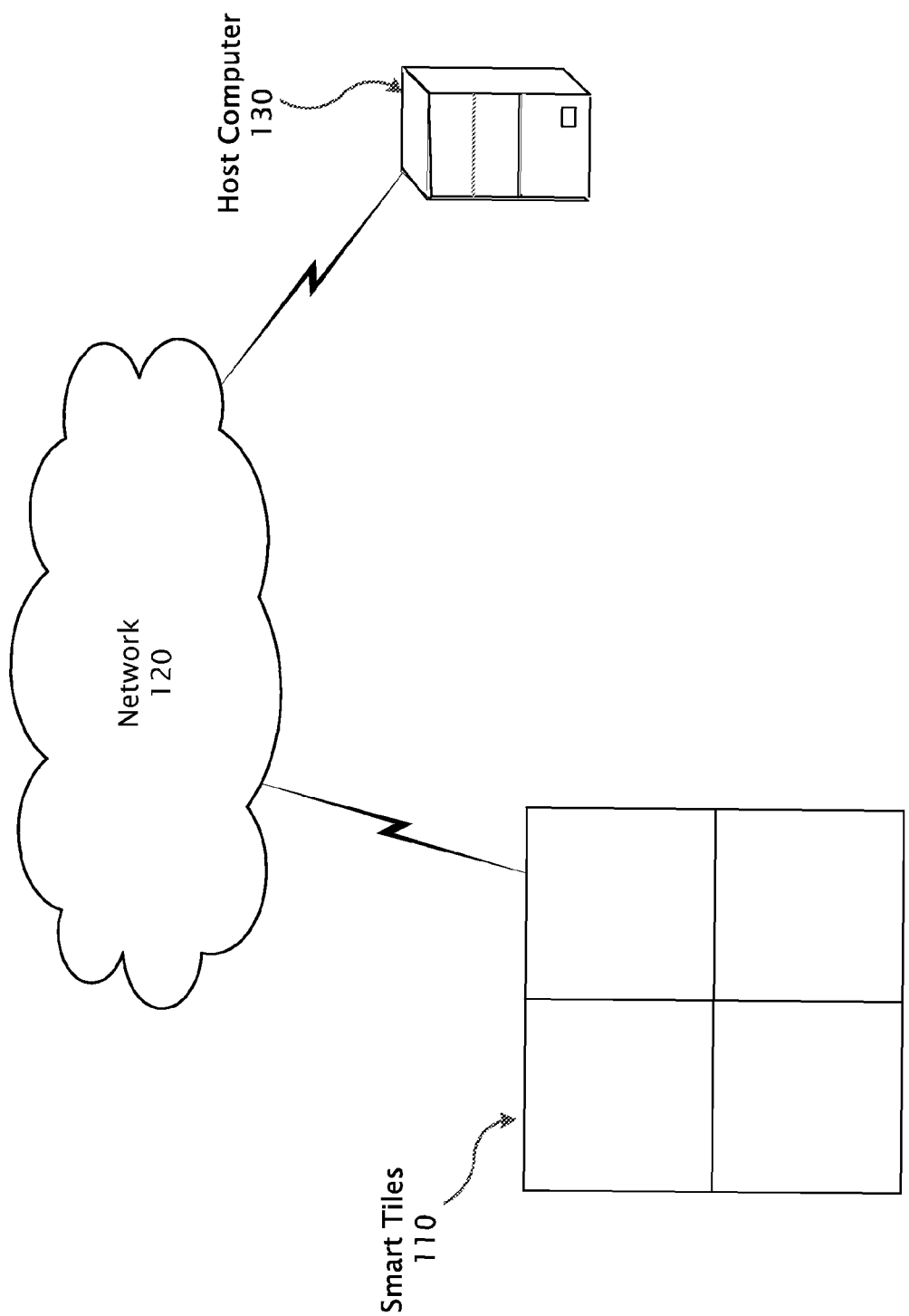
FIG. 1 is an example of a system on which Smart Tiles may be implemented according to one embodiment.

A more particular description of certain embodiments of Smart Tiles may be had by references to the embodiments shown in the drawings that form a part of this specification, in which like numerals represent like objects.

FIG. 1 is an example of a system on which Smart Tiles may be implemented.

Network 120 may include Wi-Fi, cellular data access methods, such as 3G or 4GLTE, Bluetooth, near-field communication (NFC), the internet, local area networks, wide area networks, or any combination of these or other means of providing data transfer capabilities. In one embodiment, Network 120 may comprise Ethernet connectivity. In another embodiment, Network 120 may comprise fiber optic connections.

Smart Tiles 110 may have sensors, microprocessors, and may have network capabilities to communicate with other Smart Tiles 110 and with Host Computer 130.

Host Computer 130 may include one or more computers, and may serve a number of roles. Host Computer 130 may be conventionally constructed, or may be of a special purpose design for processing data obtained from Smart Tiles 110. One skilled in the art will recognize that Host Computer 130 may be of many different designs and may have different capabilities.

Figure 2:
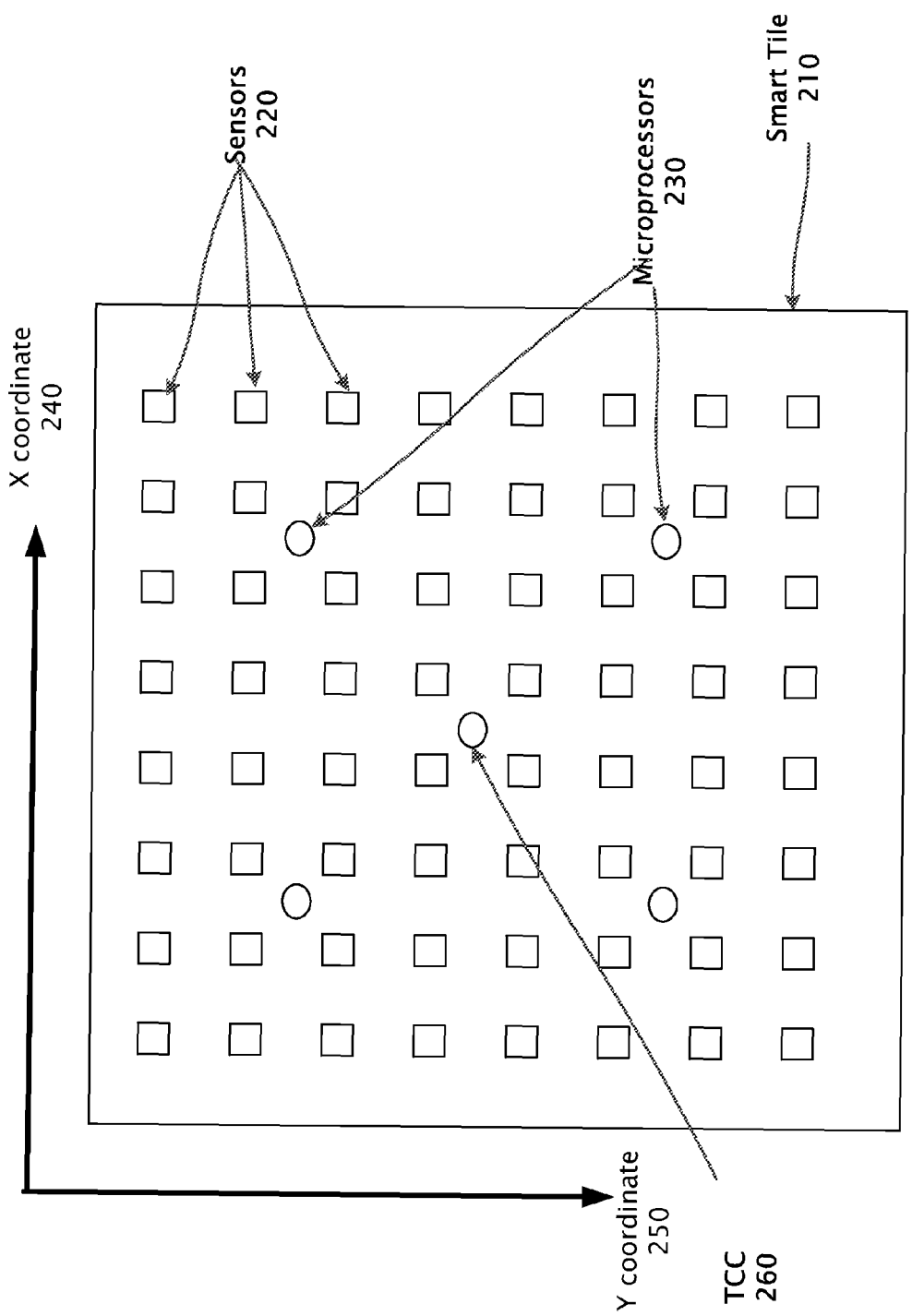
FIG. 2 is a block diagram of a Smart Tile according to one embodiment.

FIG. 2 is a block diagram of a Smart Tile 210 according to one embodiment. Smart Tile 210 may have Sensors 220 distributed across it. Sensors 220 may measure vertical pressure, lateral pressure, temperature, light, moisture, sound, or other data of interest. Sensors 220 may also comprise cameras, and provide a video signal.

Sensors may be addresses by an X coordinate 240 and a Y coordinate 250. This may allow Host Computer 130 to analyze received readings based on sensor location ("address"). For example, a sensor may be identified by a row and column number of the sensor in a grid of sensors.

Microprocessors 230 may connect to and collect data from a group of Sensors 220. Multiple Microprocessors 230 may be used on one tile, which may allow reading sensors at a higher scan cycle rate.

In one embodiment, a 60 $cm^2$ Smart Tile 210 may be used. Sensors 220 may be laid out in a grid, spaced 5 mm apart, giving 14,400 sensors per tile. Smart Tile 210 may be configured with four sections, each covering one quarter of Smart Tile 210. A Microprocessor 230 may be used for each quarter-tile ("Qtile"), and each may receive data from 3600 Sensors 220. Each Smart Tile 210 may have a central processor 260 (TCC), which may gather, correlate, and calibrate readings from four QTiles. The TCC 260 may then communicate with other Smart Tiles 210 or with Host Computer 130.

In one embodiment, QTile sensors may be arranged in a 60 column by 60 row grid. Each row of sensors may include a pull-up resistor to a Vcc of 3.3 v, and a pull-down resistor for each column. Column lines may normally be at Vcc. A column may be grounded, and sensors from that column may be read, using four 16-channel analog-to-digital convertors (ADCs). One scan cycle may include each column being driven to ground and corresponding sensors measured. In another embodiment, Vcc may be 5v. One having skill in the art will recognize that different numbers of rows and columns may be used and other ways of measuring a sensor's status may be used. One having skill in the art will also recognize that various sensor technologies may be used, and various voltages may be targeted as Vcc.

In one embodiment, there may be a synchronization server ("sync server"), which may be implemented as a software component or as a hardware component. Host Computer 130 may provide a sync server service. A sync signal may be received by a tile, and add a local time span to add a time signal to data transmitted back to Host Computer 130. Host Computer 130 may then use this synchronized time data to merge the data received. Analysis of the data may allow Host Computer 130 to calculate and notify tiles of automatically generated thresholds or other metrics to refine further data collected.

In one embodiment, sensor readings that have not changed since a previous reading may not be sent to the TCC 260, which may reduce an amount of data transferred. A buffer may be used to hold a previous reading for each sensor. In one embodiment, a programmable range may be used to determine how large a difference between readings would be filtered and not sent. In another embodiment, sensor data may be compressed to reduce communication requirements. In yet another embodiment, a timing of scan cycles may be varied to reduce communication requirements. One having skill in the art will recognize that many different techniques may be used to reduce data communication requirements.

One having skill in the art will recognize that many other sizes, numbers of sensors, and numbers of microprocessors may be used.

Figure 3:
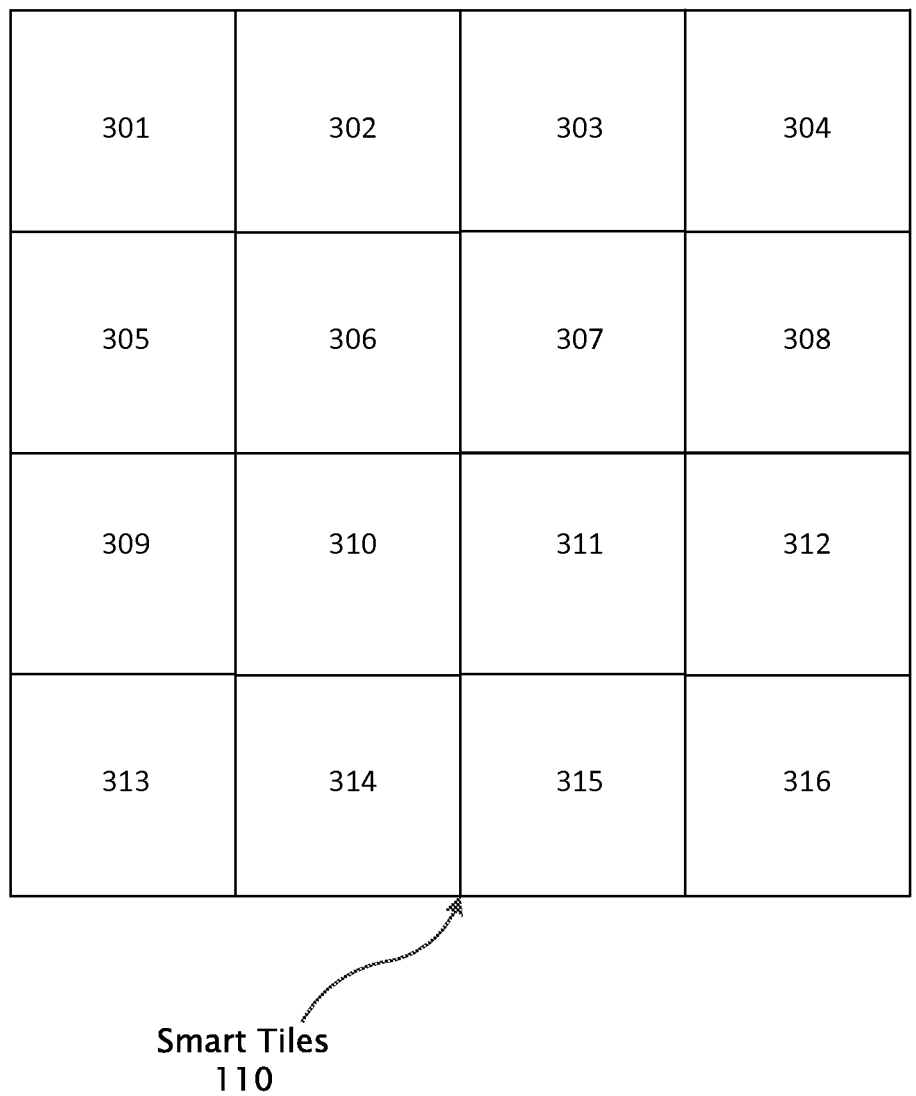
FIG. 3 is a block diagram illustrating input to a Smart Tiles server according to one embodiment.

FIG. 3 illustrates several Smart Tiles 110 used together. Smart Tiles 301-316 may be coupled to allow sensor signals to pass. This coupling may include networking, such as Ethernet, infrared transmitters and receivers, or other ways of communication. Smart Tiles 301-316 may each obtain a unique identifier, such as a MAC address, to use when communicating with each other and with Host Computer 130.

In one embodiment, Smart Tiles 110 may vary in orientation as they are placed. For example, Smart Tile 306 may have an X coordinate 240 increasing west to east based on placement on a floor, while Smart Tile 302 may be oriented with a 90 degree compared to Smart Tile 301, and thus have X coordinate 240 increasing north to south. Smart Tile 306 may collect identification data from border Smart Tiles 302, 305, 307, and 310 and may submit the collected data to Host Computer 130. This collected data may then be analyzed by Host Computer 130, which may determine a different orientation held by Smart Tile 302, and may instruct Smart Tile 302 to adjust by virtually turning 90 degrees. This may allow a dynamic fixing of orientation differences after tiles are placed.

Figure 4:
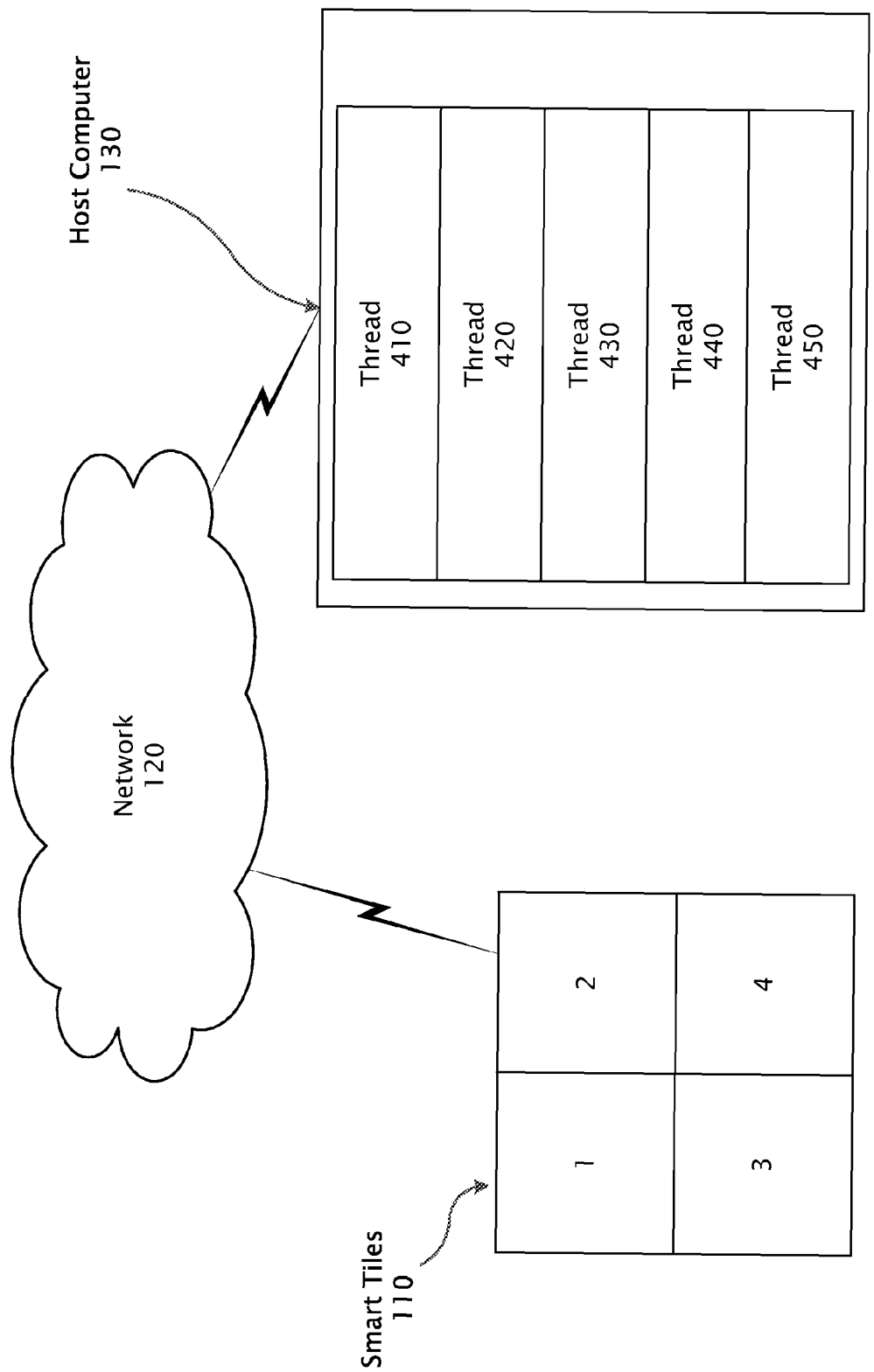
FIG. 4 is a block diagram illustrating threading considerations according to one embodiment.

FIG. 4 is a block diagram illustrating threading considerations according to one embodiment. Smart Tiles 110 1, 2, 3, and 4 may each communicate with Host Computer 130. Host Computer 130 may have a Thread 410 to receive input from Smart Tile 110 1, Thread 420 to receive input from Smart Tile 110 2, Thread 430 to receive input from Smart Tile 110 3, and Thread 440 to receive input from Smart Tile 110 4. Thread 450 may stitch each of the inputs together, which may provide a coherent picture of the data, so that pressure readings spread across tiles may be analyzed.

For example, if a person is walking from left to right across Smart Tiles 110 1 and 2, Thread 410 may receive input from Smart Tile 110 1, while Thread 420 may receive input from Smart Tile 110 2. Each of those inputs may include information about a sensor reading, a row, and a column. Thread 450 may combine rows from Smart Tile 110 1 and 2, so that an analysis may be performed for the entire length of the walk rather than just the segments done on Smart Tiles 110 1 and 2. If the person steps on the boundary between Smart Tiles 110 1 and 2, the data from each tile separately may not be sufficient to perform an analysis, but Thread 450 may allow an analysis of gait to be completed for the entire walk.

In another embodiment, a combination of gait analysis and image recognition may be used to identify a person walking on one or more tiles.

Figure 5:
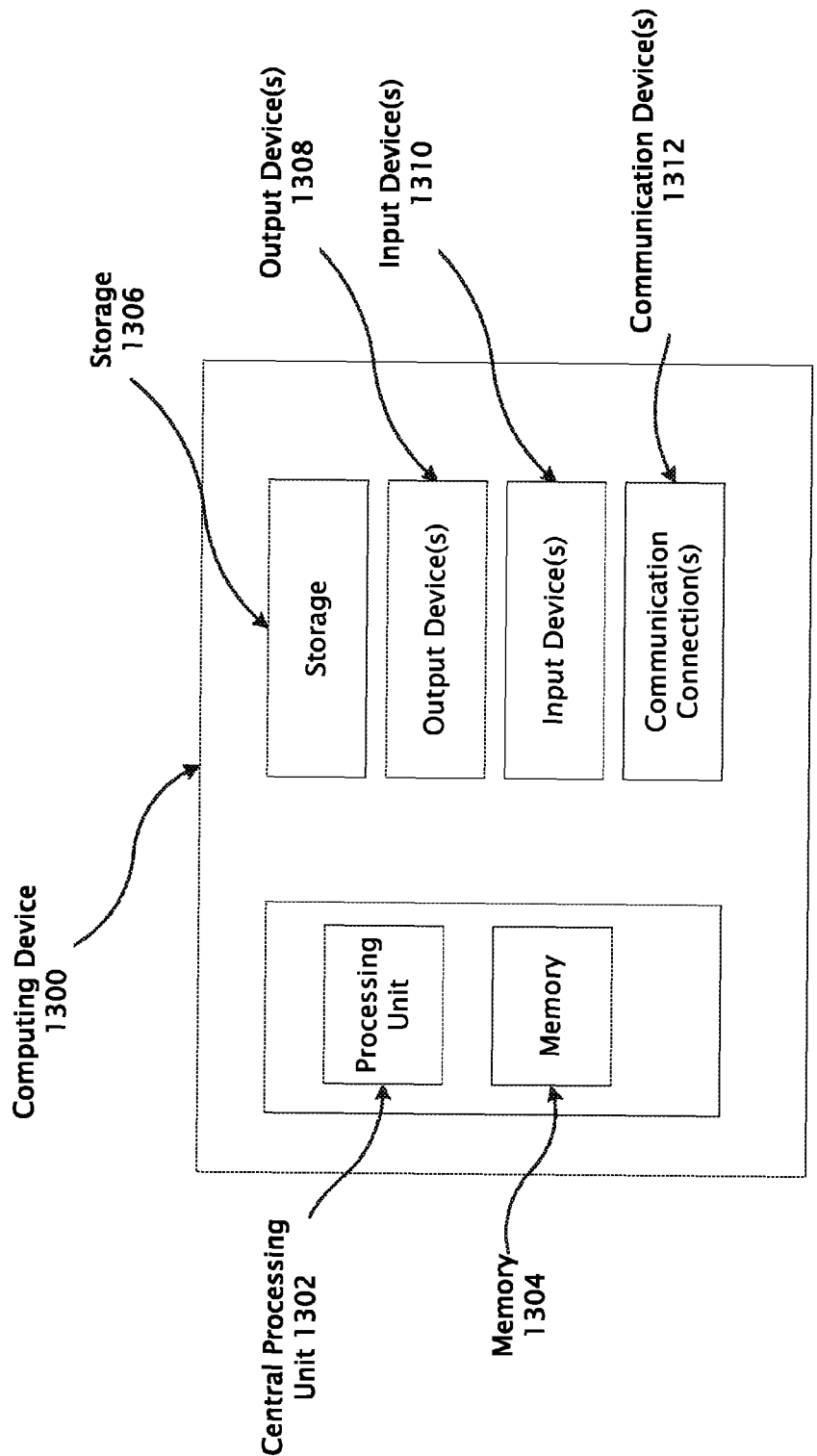
FIG. 5 illustrates a component diagram of a computing device according to one embodiment.

FIG. 5 illustrates a component diagram of a computing device according to one embodiment. The Computing Device (1300) can be utilized to implement one or more computing devices, computer processes, or software modules described herein, including, for example, but not limited to a Smart Tile 210 or a Host Computer 130. In one example, the Computing Device (1300) can be utilized to process calculations, execute instructions, receive and transmit digital signals. In another example, the Computing Device (1300) can be utilized to process calculations, execute instructions, receive and transmit digital signals, receive and transmit search queries, and hypertext, compile computer code suitable for Smart Tiles 110 or Host Computer 130. The Computing Device (1300) can be any general or special purpose computer now known or to become known capable of performing the steps and/or performing the functions described herein, either in software, hardware, firmware, or a combination thereof.

In its most basic configuration, Computing Device (1300) typically includes at least one Central Processing Unit (CPU) (1302) and Memory (1304). Depending on the exact configuration and type of Computing Device (1300), Memory (1304) may be volatile (such as RAM), nonvolatile (such as ROM, flash memory, etc.) or some combination of the two. Additionally, Computing Device (1300) may also have additional features/functionality. For example, Computing Device (1300) may include multiple CPU's. The described methods may be executed in any manner by any processing unit in computing device (1300). For example, the described process may be executed by both multiple CPU's in parallel.

Computing Device (1300) may also include additional storage (removable and/or non-removable) including, but not limited to, magnetic or optical disks or tape. Such additional storage is illustrated in FIG. 5 by Storage (1306). Computer readable storage media includes volatile and nonvolatile, removable and non-removable media implemented in any method or technology for storage of information such as computer readable instructions, data structures, program modules or other data. Memory (1304) and Storage (1306) are all examples of computer readable storage media. Computer readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can accessed by computing device (1300). Any such computer readable storage media may be part of computing device (1300).

Computing Device (1300) may also contain Communications Device(s) (1312) that allow the device to communicate with other devices. Communications Device(s) (1312) is an example of communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. The term computer-readable media as used herein includes both computer readable storage media and communication media. The described methods may be encoded in any computer-readable media in any form, such as data, computer-executable instructions, and the like.

Computing Device (1300) may also have Input Device(s) (1310) such as keyboard, mouse, pen, voice input device, touch input device, etc. Output Device(s) (1308) such as a display, speakers, printer, etc. may also be included. All these devices are well known in the art and need not be discussed at length.

Those skilled in the art will realize that storage devices utilized to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a digital signal processor (DSP), programmable logic array, or the like.

While the detailed description above has been expressed in terms of specific examples, those skilled in the art will appreciate that many other configurations could be used. Accordingly, it will be appreciated that various equivalent modifications of the above-described embodiments may be made without departing from the spirit and scope of the invention.

Additionally, the illustrated operations in the description show certain events occurring in a certain order. In alternative embodiments, certain operations may be performed in a different order, modified or removed. Moreover, steps may be added to the above described logic and still conform to the described embodiments. Further, operations described herein may occur sequentially or certain operations may be processed in parallel. Yet further, operations may be performed by a single processing unit or by distributed processing units.

The foregoing description of various embodiments of the invention has been presented for the purposes of illustration and description. It is not intended to be exhaustive or to limit the invention to the precise form disclosed. It is intended that the scope of the invention be limited not by this detailed description, but rather by the claims appended hereto. The above specification, examples and data provide a complete description of the manufacture and use of the invention. Since many embodiments of the invention can be made without departing from the spirit and scope of the invention, the invention resides in the claims hereinafter appended.

The invention claimed is:

1. A smart tile system, comprising:
 a tile, comprising:
  a plurality of sensors, wherein the sensors are the sensors are laid out in equally spaced rows and equally spaced columns, and the rows are spaced between 0.3 cm and 1 cm apart;
  a first processor, the first processor coupled to the sensors enabling the first processor to receive readings of the sensors; and
  a communications device to send the readings of the sensors to a host computer.

2. The smart tile system of claim 1, wherein the plurality of sensors is pressure sensors.

3. The smart tile system of claim 1, wherein the plurality of sensors comprise sensors selected from a group containing vertical pressure, lateral pressure, temperature, light, moisture, sound, and cameras.

4. A smart tile system, comprising:
 a tile, comprising:
  a plurality of sensors, wherein the sensors are the sensors are laid out in equally spaced rows and equally spaced columns, and the columns are spaced between 0.3 cm and 1 cm apart;
  a first processor, the first processor coupled to the sensors enabling the first processor to receive readings of the sensors; and
  a communications device to send the readings of the sensors to a host computer.

5. The smart tile system of claim 4, wherein the plurality of sensors is pressure sensors.

6. The smart tile system of claim 4, wherein the plurality of sensors comprise sensors selected from a group containing vertical pressure, lateral pressure, temperature, light, moisture, sound, and cameras.

* * * * *